United States Patent [19]

Raemer

[11] Patent Number: 4,648,396
[45] Date of Patent: Mar. 10, 1987

[54] RESPIRATION DETECTOR

[75] Inventor: Daniel B. Raemer, Brookline, Mass.

[73] Assignee: Brigham and Women's Hospital, Boston, Mass.

[21] Appl. No.: 730,158

[22] Filed: May 3, 1985

[51] Int. Cl.$^4$ .............................................. A62B 7/00
[52] U.S. Cl. ............................... 128/204.22; 128/664; 128/719; 250/343; 356/51
[58] Field of Search ...................... 128/204.22, 204.23, 128/664, 665, 670, 716, 719, 724, 736; 250/340, 343, 573, 576; 356/51

[56] References Cited

U.S. PATENT DOCUMENTS

| | | | |
|---|---|---|---|
| 3,316,902 | 5/1967 | Winchel et al. | 128/204.23 |
| 3,922,551 | 11/1975 | Williams | 250/343 |
| 4,011,859 | 3/1977 | Frankenberger | 128/719 |
| 4,050,823 | 9/1977 | Frankenberger | 356/51 X |
| 4,067,320 | 1/1978 | Olsson et al. | 128/719 |
| 4,202,352 | 5/1980 | Osborn | 128/719 |
| 4,289,142 | 9/1981 | Kearns | 128/716 |
| 4,350,166 | 9/1982 | Mobarry | 128/664 |
| 4,366,821 | 1/1983 | Wittmaier et al. | 128/719 |
| 4,370,553 | 1/1983 | Waycaster et al. | 250/343 |
| 4,446,869 | 5/1984 | Knodle | 128/716 |
| 4,537,190 | 8/1985 | Caillot et al. | 128/204.22 |

OTHER PUBLICATIONS

Hewlett-Packard Journal of Sept. 1981, pp. 3-2.
Article from Health Devices, pp. 204-220, Jul. 1981.
Article from *Journal of Thoracic and Cardiovascular Surgery*, vol. 4, No. 5, of May 1961.
Article from *Biomedical Instrumentation* by Weiss, published in 1973, pp. 151-157.
Hill, D. W. and Powell, T., *Non-Dispersive Infra-Red Gas Analysis in Science*, pp. 30-32, 43-55 (Plenum Press 1968).
Smith, R. A. et al., *The Detection and Measurement of Infrared Radiation*, pp. 251, 318-320, 359-360 (Clarendon Press 1958).
Laxminarayan, S. et al., "Sudden Infant Death Syndrome: A Digital Computer-Based Apnoea Monitor," *Medical and Biological Engineering and Computing*, vol. 21, pp. 191-196 (Mar. 1983).
Davis, A., "Infrared Spectra Correlation of Plastics and Resins," in *Process in Infrared Spectroscopy*, vol. 1, Szymanski, H. (Ed.), pp. 17-33 (Plenum Press 1961).
Wolfe, W. L., *Handbook of Military Infrared Technology*, pp. 49-50, 325-326, 458-459, 498-499, Office of Naval Research (1965).
Brochure, "The Last Vital Sign . . . " of TriMed, Inc., describing the TriMed 510 Respiration Monitor (undated).
Brown, E. S. et al., "Respiratory Carbon Dioxide and Gas Flow Measurements, in Anesthesia," in Clinical Anesthesia, Artusio, J. F., Jr. (Ed.), pp. 36-59 (F. A. Davis Co., 1964).

*Primary Examiner*—Stephen F. Husar
*Attorney, Agent, or Firm*—Saidman, Sterne, Kessler & Goldstein

[57] ABSTRACT

An improved method and apparatus for apnea detection is disclosed which features an infrared source and detector pair disposed on opposite sides of a cuvette through which the gas stream inhaled and exhaled by a patient is passed. The amount of $CO_2$ in the exhaled stream is compared with that in the inhaled stream. Where the difference is greater than a predetermined amount, a breath is taken to be detected, thus avoiding the necessity of calibration of the apparatus against any absolute reference standard. The apparatus is disclosed in an inexpensive, readily manufacturable embodiment which is nevertheless highly immune to noise and highly sophisticated in the signal processing circuitry employed in detection of breathing. The apparatus additionally provides signals indicating obstruction in or detachment of the lines connecting the patient to the apparatus.

20 Claims, 4 Drawing Figures

RESPIRATION DETECTOR

FIELD OF THE INVENTION

This invention relates to a device which provides a substantially continuous indication of the well-being of a patient. More particularly, the invention provides a detector of respiration (occurrence of breathing) which is highly accurate in use, yet which is relatively uncomplicated and inexpensive, and highly reliable and foolproof as compared to systems in the prior art.

BACKGROUND AND OBJECTS OF THE INVENTION

It has long been recognized in the anesthetic and other health-care related arts that monitoring respiration is a very reliable method of determining whether a patient is still alive, and moreover one which provides an instant indication of trouble, as compared with other life signs which take longer periods to depart from normal values. Such an indication is of great interest with patients undergoing surgery or in other life-threatening situations, and in connection with infants who, as is well-known, are subject to cessation of breathing (apnea) for no apparent cause. Therefore, it is desirable that means be provided for monitoring the continued breathing of an individual.

One method of monitoring breathing which has been extensively employed in the prior art involves monitoring the difference in carbon dioxide ($CO_2$) content between an individual's inspired and expired gas streams. It is impossible to breathe without the $CO_2$ content of the expired gas stream varying from that of the inspired gas stream by at least about 2%.

The prior art has recognized the above, yet applicant is aware of no system in the prior art which simply monitors the relative $CO_2$ content of the inspired stream and that of the expired stream and uses these to provide an indication of proper breathing or not, as the case may be. Instead, the prior art, as exemplified by the Hewlett-Packard Model 47210A capnometer, has tended toward systems of ever-increasing complexity and cost, providing in many cases values for the absolute amount of $CO_2$ present in the expired stream, which is unnecessary for a life monitor. Applicant has realized that all that needs to be detected is the relative difference in the $CO_2$ contents of the inspired and expired streams.

It seems, therefore, that a need exists in the art for a simplified and improved respiration monitor of reduced complexity and cost, which operates by simply comparing the relative $CO_2$ contents of the inspired and expired gas streams, and to provide such is accordingly an object of the invention.

The prior art has generally monitored the amount of $CO_2$ in a gas stream using infrared absorption measurement techniques. According to this technique, an infrared light source radiates through a cuvette having spaced parallel windows in which is enclosed a sample of the gas to be monitored. The radiation then falls on a suitable detector, typically a Golay cell such as Beckman Instruments' Model LB-2, which is highly sensitive to acoustic noise, or a PbSe photodetector, which is very sensitive to low-frequency noise, a significant defect in the environment of this invention.

It is an object of this invention to avoid use of these and other non-optimal detectors.

According to one aspect of the invention, radiation is monitored by a thermopile (a combination of a number of individual thermistors, so as to be very sensitive to small temperature changes). Such thermopiles are useful even at low frequencies and in connection with D.C., unlike the other detector types mentioned.

As in the prior art, the detector output is monitored. As infrared radiation of particular wavelengths is preferentially absorbed by carbon dioxide, the output of a detector sensitive to those wavelengths provides an inverse indication of the relative amount of $CO_2$ in the gas stream. By calibration using a sample of known concentration, or possibly by other methods, the detector can be made to yield quite accurate results; however, as mentioned above, the object of the invention is not so much to provide intrinsically accurate results concerning the actual amount of $CO_2$ present in a patient's exhaled gas stream, but merely to determine whether the patient is breathing. Therefore, according to the invention, calibration is ordinarily not performed, and the instrument is simply operated so as to detect variation in the $CO_2$ contents of the inspired and expired gas streams.

Accordingly, it is an object of the invention to provide a respiration detector which operates by detecting the differences between the $CO_2$ concentration of inspired and expired gas streams, by providing a source of infrared radiation disposed in juxtaposition to a cuvette containing the gas stream to be measured, and by monitoring the output of a thermopile disposed opposite the infrared source on the other side of the cuvette, which does not require calibration for proper operation.

It will be appreciated by those skilled in the art that measurement of the $CO_2$ content of a sample by radiation adsorption techniques is subject to error due to a number of factors. Though as mentioned above, the invention of the applicants is not so much concerned with measurement of the absolute value of the $CO_2$ in the patient's breath as between the relative difference in $CO_2$ content between the inspired and expired streams, it is nevertheless desirable that the instrument be operated in the optimal fashion and furthermore that it be enabled to operate under less than ideal conditions which may include, for example, clouding of the windows through which the infrared beam passes due to humidity, temperature drift and the like. Further, it is desirable that the instrument measure the relative difference in the $CO_2$ contents of the streams accurately regardless of their absolute value, i.e. whether the difference is between 0 and 3% $CO_2$ or between 6 and 9%. Finally, it is desirable that the absolute amount of radiation incident on the thermopile be substantially constant so that it can be well matched to the input value which provides the greatest dynamic range in the thermistor output signal.

For all of the above reasons, it is desirable that means be provided to regulate the intensity of the radiation falling on the thermopile, so as to compensate the system for all the sources of possible error discussed above.

In the preferred embodiment, this is achieved by provision of a feedback loop connecting the output of the thermopile with the power supply which is used to operate the source of infrared radiation. Use of feedback in a loop having a low pass filter therein ensures that variation in the inspired and expired gas stream will not cause the bulb output to vary, while ensuring that the mean output of the thermopile is maintained at a substantially constant level, thus compensating for all the sources of error just discussed.

The selection of the infrared source has also been a source of some difficulty and expense in the prior art. The applicant has realized that, by using certain ordinary incandescent lamp bulbs, an adequate amount of infrared light of suitable wavelength is provided to enable suitable detection, thus further simplifying and reducing the cost of the apparatus of the invention.

It is therefore an object of the invention to further simplify and reduce the cost of the apparatus of the invention by using an inexpensive source of infrared radiation.

The prior art has also used costly sapphire windows for the windows of the cuvette. It is an object of the invention to avoid use of such materials.

It will be appreciated by those skilled in the art that the output of typical thermopiles is a relatively small voltage, usually on the order of millivolts. It will further be appreciated by those skilled in the art that in the typical hospital operating room environment of today, there are frequently a large number of electronic devices, some of which may not be properly shielded. Accordingly, it is desirable that the instrument be designed in such a way as to be less sensitive to electromagnetic noise than otherwise, and furthermore that the signal processing circuitry to which the thermopile is connected be enabled to differentiate between noise and signal insofar as reasonably possible, given the goals of simplicity and low cost, as discussed above, and such is accordingly an additional object of the invention.

It is furthermore desirable that the gas stream be monitored as closely to the patient as possible, to obtain accurate results. Accordingly, the sensor of the respiration monitor of the invention should be lightweight, so as to be attachable directly to flexible tubing connected closely to the patient while still achieving the other objects of the invention discussed above, and such is accordingly an additional object of the invention.

SUMMARY OF THE INVENTION

The present invention fulfills the needs of the art and the objects of the invention mentioned above by its provision of a simple and reliable, yet highly accurate and useful, respiration detector. The detector according to the invention comprises one or more common light bulbs juxtaposed to a window in a housing. The housing is shaped so that this window and an opposing window, behind which is disposed a thermopile, may be simply "clipped" over corresponding windows in a cuvette connected to an endotracheal tube, to a source of inspired gas and to a receptacle for expired gas. The thermopile is connected to an instrumentation preamplifier which is carried directly in the housing so as to amplify the small voltage signals output by the thermopile as soon as possible in order to minimize the risk of any interference. The sensor and preamplifier assembly is additionally shielded against electromagnetic interference. The output of the amplifier also is provided to the light bulbs which provide the infrared radiation, for feedback purposes, to ensure that the baseline level of the system remains relatively constant over time. The system is connected to relatively straightforward signal processing circuitry which includes means for differentiating the input signal. Such differentiation provides an indication of the rate at which the $CO_2$ concentration changes, which can be used to differentiate between changes in signal level caused by variation in the $CO_2$ content due to breathing and relatively spike-like noise pulses, which is the more common type of high amplitude noise. Low amplitude noise is distinguished from breath signals by requiring that the breath signal exceed a predetermined amplitude before a breath is considered to be detected. The differentiated breath signal plus the expired breath signal and the relative time of events determined therefrom are supplied to signal processing circuitry which operates according to predetermined rules of logic to generate an alarm signal when cessation of breathing has been correctly detected.

BRIEF DESCRIPTION OF THE DRAWINGS

The invention will be better understood if reference is made to the accompanying drawings in which.

DESCRIPTION OF THE PREFERRED EMBODIMENTS

Figure 1:
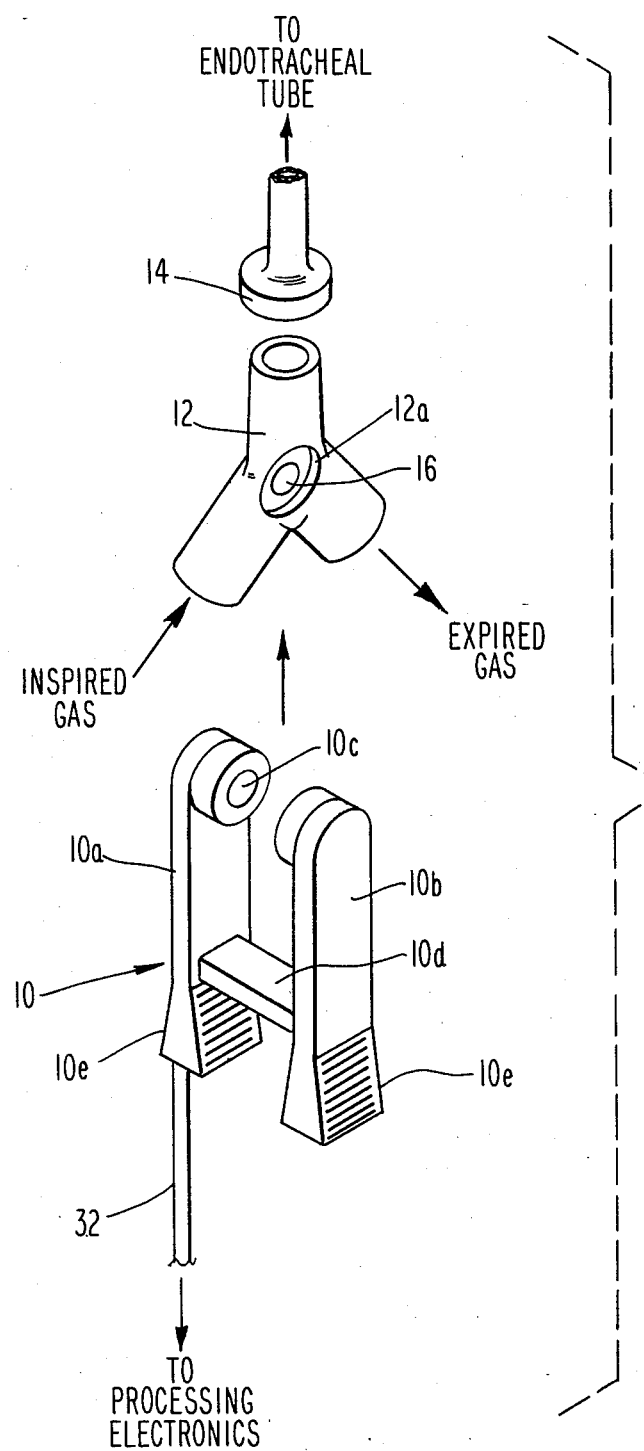
FIG. 1 shows respective views of the sensor assembly according to the invention and how it may be attached to a "wye"-shaped cuvette in the patient's gas circuit.

FIG. 1 shows the sensor assembly 10 according to the invention which is generally H-shaped. The assembly 10 comprises a unitary housing molded of a plastic material and typically comprising two parallel members 10a and 10b having windows 10c facing one another. Behind one of the windows is disposed a thermopile and behind the other is disposed the source of infrared radiation. The crossbar 10d of the housing 10 is provided with some slight amount of flexibility so that, by an operator placing his fingers on opposed pads 10e on the lower ends of the parallel members 10a and 10b and exerting pressure thereagainst, the upper ends can be sprung slightly outwardly to permit the ends having the windows 10c to be inserted into recesses 12a formed in the mating cuvette 12.

The cuvette 12 in the embodiment shown is wye-shaped. One leg of the wye is connected to a source of inspired gas, which may be anesthetic or the like, including air, one to a receptacle for expired gas, and one to a fitting 14 to which is connected an endotracheal tube connected to the patient. Recesses 12a with windows 16 formed therein are provided on either side of the cuvette 12 so that when the sensor housing 10 is assembled to the cuvette 12, the windows 10c in the ends of housing 10 are juxtaposed directly to the windows 16 in the cuvette, so that a sample of the gas in the cuvette is interposed between the thermopile and the infrared source.

Figure 2:
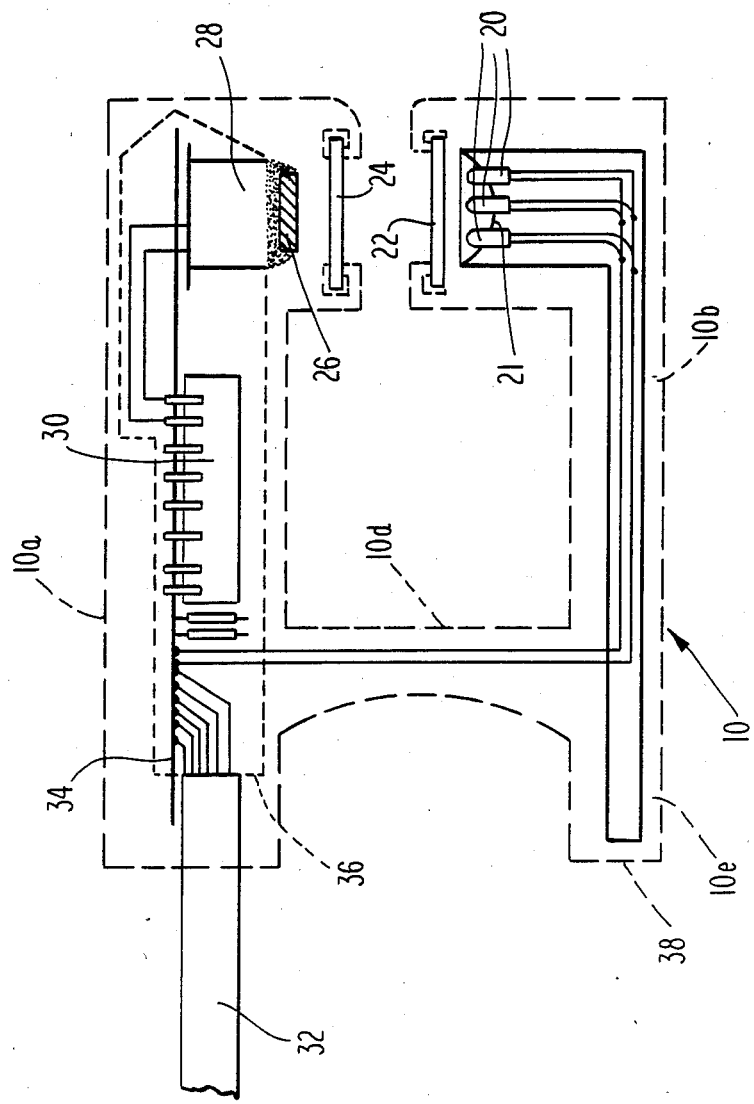
FIG. 2 shows a cross-sectional view of the sensor assembly.

FIG. 2 shows a cross-sectional schematic view of the sensor housing 10 and its contents. Preferably, the entire assembly is enclosed in a molded plastic housing with appropriate recesses formed therein to hold the various components shown. At 20 are shown a plurality of light bulbs which provide infrared radiation. These may be the Model 7153-T7/8 from Lamp Technology, Incorporated of Farmingdale, N.Y. They are disposed behind a first plastic window 22 which may be made of polycarbonate on the order of 1-5 mils thick to ensure good infrared light transmission. A wide variety of polycarbonate plastics are suitable. Behind the bulbs 20 is disposed a parabolic mirror 21 which ensures that the light generated by the bulbs is all directed toward a thermopile 28, increasing the sensitivity of the instrument for a given power consumption. (In this connection, the applicants have found that the optimum source-to-detector distance is 2.5 cm.) A similar window 24 is formed in the opposed portion of the H-shaped sensor housing 10, behind which is disposed an interference filter 26, and the thermopile 28. The interference filter, which may be a 4.25 micron narrow-band interference filter from Optical Coating Laboratory, Inc. of Santa Rosa, Ca., is used to prevent incidence of radiation other than of 4.25 micron wavelength, which is selectively absorbed by $CO_2$, on the thermopile 28. The thermopile 28, as mentioned above, comprises a number of individual thermocouples in series so as to generate a detectable voltage proportional to the amount of infrared radiation falling thereon. The Model 2M from the Dexter Research Company of Dexter, Mich. has been found suitable. Preferably, the thermopile housing is sealed after assembly and filled with a gas such as argon, which does not absorb infrared radiation. As discussed above, infrared radiation is absorbed by $CO_2$; therefore, monitoring of the voltage signal generated by the thermopile provides comparison of the $CO_2$ content of the inspired gas with that of the expired gas. If the comparison indicates a difference in $CO_2$ content equal at least to a predetermined percentage and certain other parameters of breathing discussed below are detected, it can safely be concluded that the patient is breathing, absorbing oxygen and exhaling $CO_2$.

The thermopile 28 is connected to a preamplifier 30. In the preferred embodiment, this may comprise a Model AD524 instrumentation amplifier or equivalents thereof. An op amp (not shown) controlling the power supply for the bulbs 20 may also be disposed within the sensor housing 10. The output signal from the preamp 30 may be fed to the op amp for low-pass or integral feedback control of the bulb output, such that the mean intensity of the radiation incident on the thermopile is maintained constant. Power is supplied to the system over a cable 32 connected to the signal processing electronics; this cable also carries the output signal from preamp 30. The thermopile, the preamp, and any additional op amp used are carried on a single printed circuit board indicated generally at 34, and the entire assembly is preferably enclosed in an electromagnetic shield 36 indicated by dotted lines. Provision of the preamplifier 30 inside the electromagnetic shield 36 with the thermopile 28 provides a reasonable measure of immunity against electromagnetic interference from other electronic instruments in the operating room.

The outline of the sensor housing is shown as well at 38. The housing may conveniently comprise a substantially identical pair of injection moldings provided with appropriate recesses to hold the various parts shown in the drawing of FIG. 2, and provided with sufficient flexibility in the bridge section of the H shape formed by the housing to allow the ends of its two legs 10a and 10b carrying the thermopile and the bulbs to be sprung apart by pressure on opposing ends of the legs.

Figure 3:
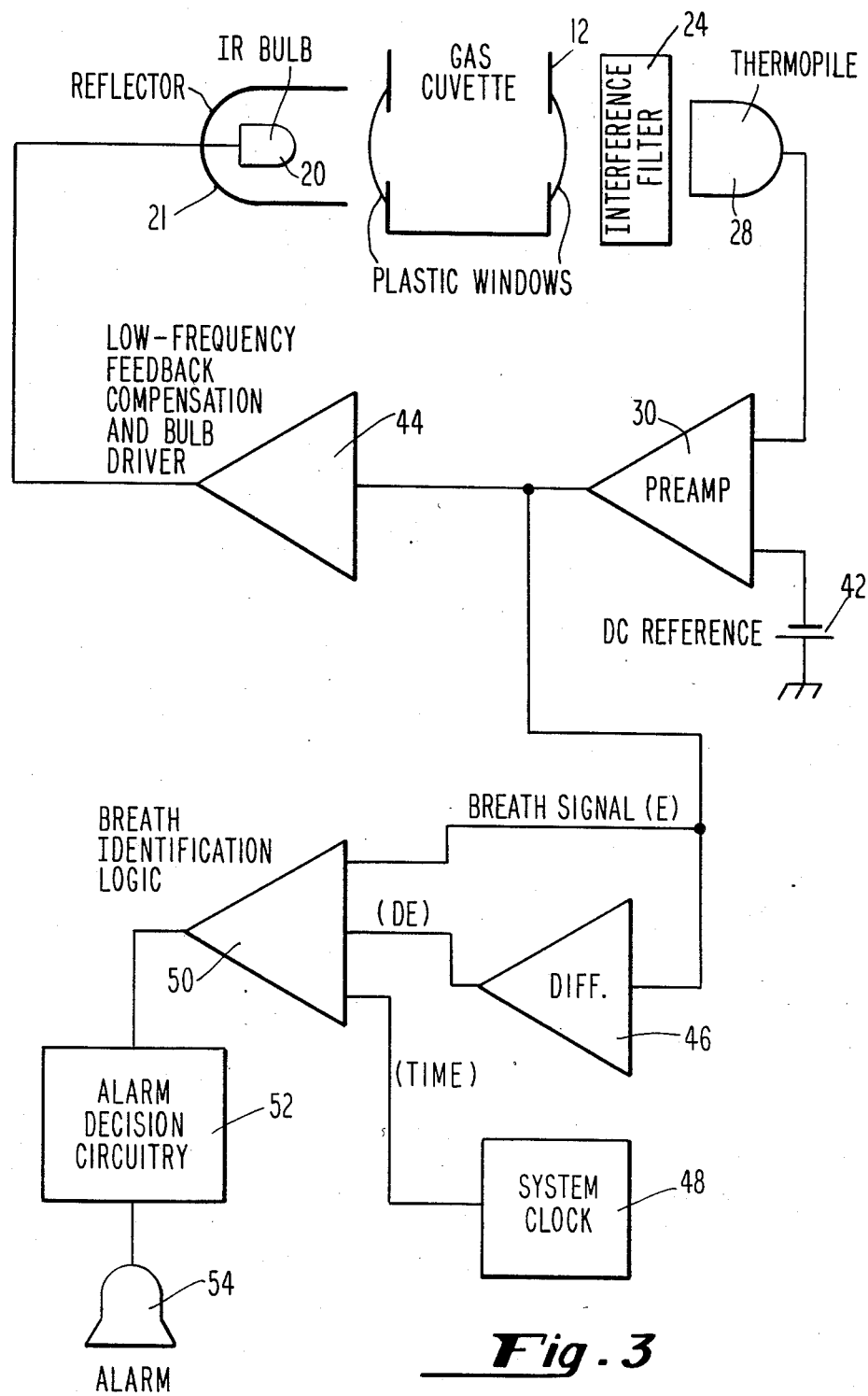
FIG. 3 shows a block diagram of the sensor and signal processing circuitry employed.

FIG. 3 shows the signal processing electronics according to the invention in block diagram form; the Figure also shows some of the components shown in FIG. 2 for completeness. A single infrared bulb 20 is shown disposed on one side of the cuvette 12; on the other side of the cuvette are disposed the interference filter 24 and the thermopile 28. The reflector 21 is also shown. The gas cuvette comprises plastic windows, preferably formed integrally, again of material which is relatively transparent to infrared radiation such as polycarbonate plastics, as described above.

The output of the thermopile is connected to preamp 30 which is D.C. referenced by a battery 42 or another voltage source connected between it and ground. This permits the output of the preamp 30 to be passed to an op amp 44 to drive the bulb 20 using feedback techniques, so that the level of radiation incident on the thermopile remains constant over time, regardless of such things as window clouding, temperature-induced component drift, and so on. The output of preamp 30 is a signal proportional to the $CO_2$ level in the patient's breath, referred to hereafter as signal E. Signal E thus includes a portion proportional to the $CO_2$ content of both the inspired and expired gas streams, which correspond respectively to the "valleys" and "peaks" in signal E. Thus monitoring of the difference between the peaks and valleys of signal E in effect provides a measure of the difference in $CO_2$ content between the inspired and expired streams.

Signal E is also supplied to a differentiator 46 in which it is differentiated; the output of differentiator 46 is referred to as the differentiated signal DE. Finally, a system clock 48 provides time signals as a third input to the breath identification logic 50, which is detailed below. The output of the logic 50 is sent to alarm decision circuitry 52 which raises an alarm when apnea is detected by sounding an alarm 54.

Those of skill in the art will recognize that, in addition to a patient's lack of breathing due to some physical irregularity, sometimes the sensor may be detached from the processing equipment, the plumbing connecting the patient with the equipment may be blocked and so on. It is also desirable to provide signals indicative of such failures, in particular, to give signals which will assist the operating room personnel in finding the cause of the alarm. The logic now to be described provides signals indicating sensor obstruction and sensor detachment, which occasionally occur.

In one embodiment of the invention which was successfully tested, the output signal E and the differentiated version thereof DE are compared by four comparators (not shown) to reference levels. These are referred to in the following as $R_{EL}$ (reference signal low), $R_{EH}$ (reference signal high), $R_{DEL}$ (reference derivative signal low) and $R_{DEH}$ (reference derivative signal high). Additionally, the source of the voltage, that is, the output of op amp 44, which drives the bulb 20, is additionally monitored to confirm that there is adequate infrared radiation incident on the thermopile to enable accurate detection. This signal is referred to as S; S is similarly compared to reference values to yield values of $R_{SL}$ (reference source voltage low) and $R_{SH}$ (reference source voltage high).

From these comparators, additional signals used by the logic are derived as follows:

$EL = E > R_{EL}$, that is, EL is true whenever the breath signal E is greater than the reference level $R_{EL}$;

$EH = E > R_{EH}$, that is, EH is true whenever the signal E is greater than $R_{EH}$;

$DEL = DE > R_{DEL}$, that is, DEL is true when the derivative DE of the signal E is greater than the reference derivative signal low level $R_{DEL}$;

$DEH = DE > R_{DEH}$, that is, DEH is true whenever the derivative DE of the signal E is greater than the reference derivative signal high level $R_{DEH}$;

$SL = S > R_{SL}$, that is, SL is true whenever the source voltage S is greater than the reference low source voltage $R_{SL}$; and $SH = S > R_{SH}$, that is, SH is true whenever the source voltage S is greater than the reference high source voltage $R_{SH}$.

The signals just defined are used by the processing circuitry as follows:

1. If SL and $\overline{SH}$ and ((DEL and not DEH) in last N ms) and EH and (EL in last M ms) and ($\overline{BREATH}$ for P ms.)
   Then BREATH According to the above equation, if the source voltage is correct (SL and $\overline{SH}$) and the derivative signal, that is, the value of the rate of change of the $CO_2$ content, is within limits (DEL and not DEH) for a specified period N, and EH is true, indicating that the peak of the $CO_2$ value is greater than the reference value $R_{EH}$ set to correspond to the anticipated $CO_2$ level of expired gas, and EL has been true for the period M (EL in last M ms), that is, that the $CO_2$ level for the inhaled stream has been below the reference level $R_{EL}$ for the period M, and BREATH has not been true for some period of time P, then the signal BREATH is generated, indicating successful detection of a breath.

The above description of the logic detection of a breath can be summarized as follows. The source voltage is first checked. The values of the derivatives are checked so as to eliminate noise as an erroneous source of $CO_2$ measurement. The peak of the $CO_2$ signal is checked against a reference level and the lower level, that is, the $CO_2$ content of the inspired air is also checked, so as to confirm that the difference in $CO_2$ gas streams between the inspired and expired level is at least equal to the difference between $R_{EL}$ and $R_{EH}$. Finally, this logic confirms that the last BREATH signal was present so as to continue to give the alarm, even if a subsequent breath is detected.

2. If $\overline{BREATH}$ for R sec then APNEA

This simply indicates that after no BREATH signal has been detected for a period of time R, the APNEA signal is raised.

3. If $\overline{SL}$ then SENSOR DETACH

This item simply indicates that if the SL signal is negative, this means that the source voltage has disappeared, ordinarily because the sensor has become detach from the cuvette.

4. If SH then SENSOR OBSTRUCT

Similarly, if SH goes high, this means the sensor is obstructed, e.g. by mucus or humidity blocking the passage of radiation, preventing adequate absorption of $CO_2$ by the thermopile.

5. If APNEA and SENSOR DETACH and $\overline{SENSOR\ OBSTRUCT}$, then APNEA ALARM and APNEA LIGHT.

Thus, if the APNEA signal is raised and the SENSOR DETACH and SENSOR OBSTRUCT signals are not raised, the APNEA ALARM signal is given. In a preferred embodiment, a light on the control box is also lit in this circumstances; hence, the APNEA LIGHT signal is also energized.

6. If APNEA and SENSOR DETACH or SENSOR OBSTRUCT, then APNEA ALARM and APNEA LIGHT.

If, on the other hand, the APNEA signal and either the SENSOR DETACH or SENSOR OBSTRUCT signals are raised simultaneously, then the light is lit but the APNEA ALARM is not energized, indicating that some other problem is present which must be corrected.

A worker of ordinary skill in the bioelectronic art would have no difficulty in designing logic circuitry to implement the above.

Figure 4:
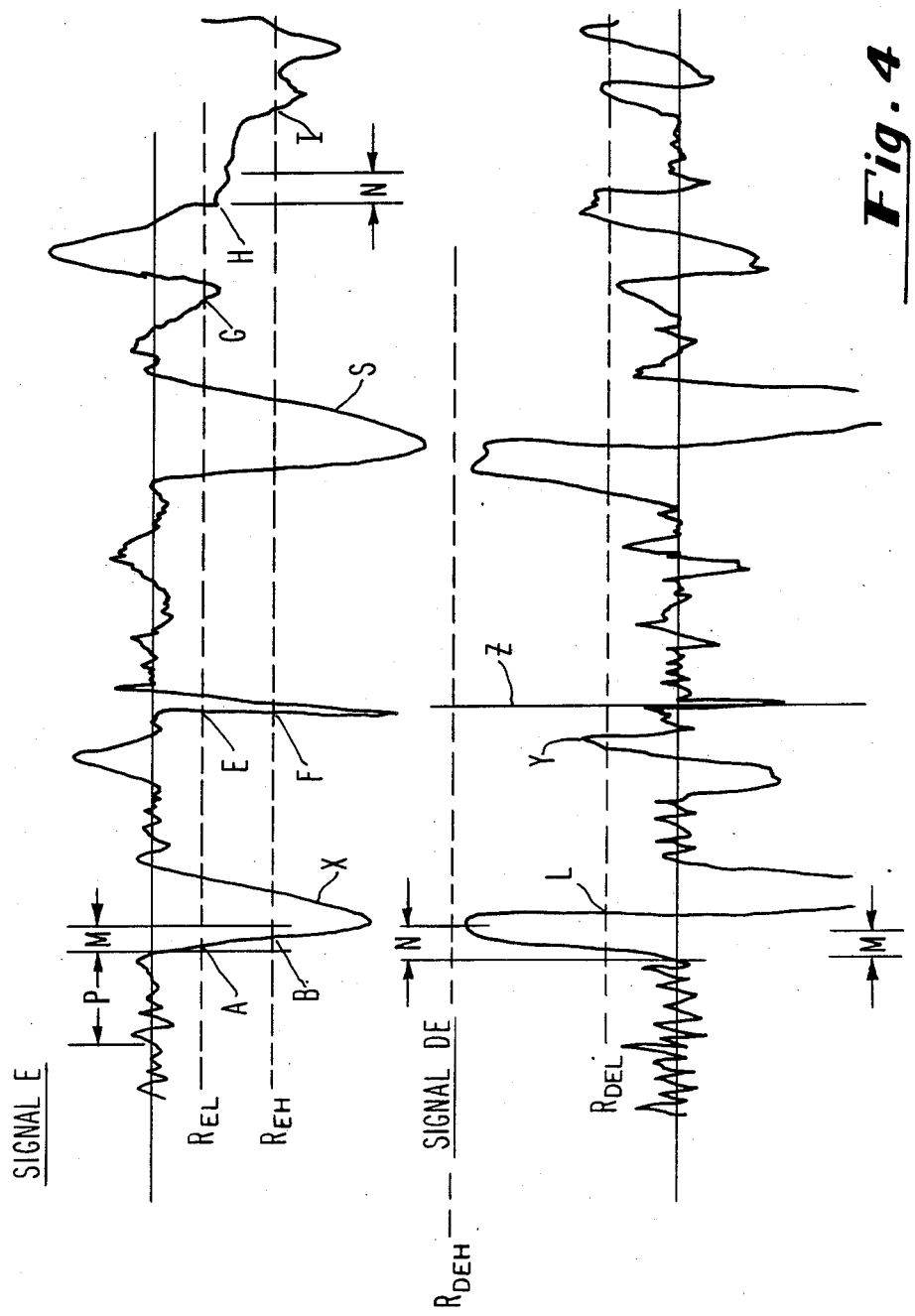
FIG. 4 shows typical waveforms obtained from the breath detector useful in understanding the way in which the signal processing circuitry interprets the signals shown.

FIG. 4 is an example of actual waveforms useful in understanding the operation of the system of the invention, in particular the logic which has just been described. The upper chart in FIG. 4 shows the signal E proportional to the voltage generated by the thermopile and the lower chart shows signal DE, the differentiated version of signal E. The reference levels $R_{EL}$ and $R_{EH}$ are shown in the upper graph as are $R_{DEH}$ and $R_{DEL}$ on the lower graph. Thus, each of the negative-going peaks on the upper graph represents a change in $CO_2$ content which might be interpreted as indicative of a breath. The first negative-going peak X is recognized as a breath because the value corresponding to the DE signal has exceeded $R_{DEL}$ but not $R_{DEH}$ in the last N ms; the E signal has gone from A to B in the last M ms; and no breath has occurred in the last P ms. Peak S is similar. By comparison, peak Y, appearing in the lower graph, would not be recognized as a breath because the amplitude criteria have not been met by the E signal. Item Z is clearly noise, as the value of the derivative signal DE exceeds the maximum amplitude $R_{DEH}$, indicating that the $CO_2$ concentration had changed too abruptly to have been a legitimate breath. Item H would not be a breath because DE exceeded $R_{DEL}$ within N ms. Again, this is due to the electrical noise. Item G would be rejected as a breath because the derivative criteria have not been met, the amplitude criteria were not met, i.e., G does not exceed $R_{EH}$, and a breath has occurred within P ms, at S. Finally, item I would be rejected as motion disturbance because it had been more than N ms. since the E signal exeeded $R_{EL}$ at H. That is, the derivative criteria again were not met.

It will be appreciated that while a preferred embodiment of the invention has been described, additional modifications and improvements thereto could be made by those skilled in the art without departure from the spirit and scope of the invention. In particular, while essentially analog signal processing circuitry has been described, microprocessor implementation is well within the skill of the art; typically, the expired signal would be converted from an analog to a digital value, possibly by a suitable converter mounted on the same printed circuit board as the preamp 30 shown in FIG. 2, so as to provide additional noise immunity. Other improvements and modifications will no doubt occur to those skilled in the art including such things as modification of the cuvette design shown, and inclusion of the cuvette within a housing carrying the signal processing and logic circuitry rather than providing a relatively lightweight portable sensor and forming the cuvette as part of the breathing tube itself, as described above. Therefore, the above exemplary description of the invention should be construed liberally and not as a limitation on the scope of the invention, which is to be limited only by the following claims.

What is claimed is:

1. An apparatus for monitoring respiration, comprising:
   means for monitoring the carbon dioxide content of a patient's expired gas stream and for monitoring the carbon dioxide content of the patient's inspired gas stream; and
   means responsive to said means for monitoring for generating an alarm signal whenever the carbon dioxide content of the expired stream does not exceed the carbon dioxide content of the inspired gas stream by a predetermined amount, whereby calibration of said apparatus for an absolute value of carbon dioxide in either of said streams is avoided.

2. The apparatus of claim 1 wherein said means for monitoring the carbon dioxide content of a patient's inspired and expired gas streams comprises an infrared source juxtaposed to one side of a cuvette containing a sample from one of said gas streams and a thermopile on the other side of said cuvette, whereby said thermopile generates an output signal proportional to the amount of infrared light incident thereon, such that variations in the output signal from said thermopile are indicative of variations in the carbon dioxide content of the sample in the cuvette.

3. The apparatus of claim 1, further comprising means for differentiating between contributions to the output signal due to carbon dioxide in said sample and noise.

4. The apparatus of claim 3 wherein said means for differentiating between contributions to the output signal due to carbon dioxide in said sample and noise comprises means for taking the time derivative of said output.

5. In combination, a sensor housing and a cuvette for use in breath monitoring apparatus, said cuvette and said sensor housing each including two windows for the passage therethrough of infrared radiation, wherein said windows are formed of a plastic material, said material and the thickness of said windows being selected so that said windows are substantially transparent to infrared light.

6. The combination of claim 5 wherein said housing is adapted to contain a thermopile and said housing additionally comprises electromagnetic shielding means for shielding said thermopile for prevention of interference by electromagnetic noise with signals generated by said thermopile.

7. The combination of claim 6 wherein said housing and said electromagnetic shielding means are adapted to further contain a preamplifier adapted to amplify an output signal generated by said thermopile.

8. The combination of claim 6 wherein said housing is adapted further to retain a source of infrared radiation within said housing such that radiation from said source is directed substantially directly at said thermopile disposed within said housing, and said cuvette and said housing are adapted to mate with one another such that radiation from said source passes through one of said windows in said housing and one of said windows in said cuvette, into said cuvette, and thence through the second of said windows in said cuvette and through the second of said windows in said housing, and is then incident on said thermopile.

9. The combination of claim 8 wherein said source of infrared radiation is one or more incandescent light bulbs.

10. The combination of claim 9 further comprising mirror means disposed behind said bulbs with respect to said detector.

11. Method of detection of a breath of a patient by monitoring the carbon dioxide content of a gas stream passing through a cuvette operatively connected to the patient, comprising the steps of:
   providing a source of infrared radiation;
   providing a detector of infrared radiation, adapted to generate a signal proportional to the amount of infrared radiation incident thereon, arranged with respect to said source and said cuvette such that infrared radiation emitted by said source passes through said cuvette and is then incident on said detector;
   monitoring the output signal generated by said detector as a function of time; and
   examining the variation of said output signal as a function of time to determine when a breath has been detected.

12. The method of claim 11 wherein said step of examining the variation of said output signal as a function of time comprises the step of taking the first derivative of said output signal and comparing said output signal and said first derivative of said output signal to predetermined limits to determine when a breath has been detected.

13. The method of claim 12 wherein detection of a breath is performed by comparing the amplitude of peaks in the output signal, indicating the level of carbon dioxide in the expired gas stream, to a reference signal value selected to be greater than the maximum level of carbon dioxide in the inspired gas stream by a predetermined amount, whereby calibration of said instrument against an absolute reference standard is eliminated.

14. In an instrument for the measurement of the amount of carbon dioxide in a expired gas sample, comprising a source of infrared radiation and a detector of infrared radiation generating a signal proportional to the amount of infrared radiation incident thereon, said source and said detector being disposed in a common housing so as to be juxtaposed to opposing windows of a cuvette containing a gas sample, the improvement which comprises providing preamplification means for the signal output by said detector and enclosing said detector and said preamplification means within a electromagnetic radiation shield within said housing, whereby external interference with the signal output by said detector is substantially eliminated.

15. In an instrument for the measurement of the amount of carbon dioxide in a expired gas sample, comprising a source of infrared radiation and a detector of infrared radiation generating a signal proportional to the amount of infrared radiation incident thereon, said source and said detector being disposed in a common housing so as to be juxtaposed to opposing windows of a cuvette containing a gas sample, the improvement which comprises providing means for controlling the mean amount of infrared radiation incident on said detector to be substantially constant over time.

16. The instrument of claim 15 wherein said means for controlling the amount of infrared radiation incident on said detector comprises a feedback loop, said loop including said detector, a low-pass filter, a power supply for said source of infrared radiation, and said source.

17. A method of detecting a breath in a patient, comprising the steps of:
- generating a breath signal varying in dependence on the amount of carbon dioxide in the patient's breath stream;
- establishing predetermined upper and lower reference signal values, corresponding to predetermined amounts of carbon dioxide in the breath stream;
- comparing the breath signal to the upper and lower predetermined reference signal values for a predetermined period of time;
- generating an inspired signal when the breath signal is less than the lower reference signal value during said predetermined period;
- generating an expired signal when said breath signal is greater than the upper reference signal during said predetermined period; and
- generating a signal indicative of detection of a breath when both said inspired and expired signals are generated during the same predetermined period of time.

18. The method of claim 17 wherein the difference between said upper and lower reference signal values corresponds to a difference in carbon dioxide content in the expired and inspired breath streams of the patient of at least about 2%.

19. The method of claim 17, wherein said breath signal is the output of a thermoelectric device generating a signal responsive to the amount of infrared radiation incident thereon, said radiation being emitted by a source controlled to emit a substantially constant amount of radiation over time, and comprising the additional step of verifying the operation of said source prior to generating said breath signal.

20. The method of claim 17, comprising the additional steps of:
- differentiating said breath signal to obtain a differential breath signal;
- comparing said differential breath signal to predetermined upper and lower limits; and
- generating the breath signal for a given predetermined period only if said differential signal does not exceed the upper limit or go below the lower limit during said given predetermined period.

* * * * *